United States Patent

Saitoh et al.

[11] Patent Number: 6,045,521
[45] Date of Patent: Apr. 4, 2000

[54] ORTHOTIC APPARATUS FOR PARAPLEGIC PATIENT

[75] Inventors: Eiichi Saitoh, Toyoake; Toyoteru Manabe; Masayasu Hayashi, both of Nagoya, all of Japan

[73] Assignee: Kabushiki Kaishi Tatematsu Seisakucho, Nagoya, Japan

[21] Appl. No.: 09/093,266

[22] Filed: Jun. 8, 1998

[30] Foreign Application Priority Data

Jun. 9, 1997 [JP] Japan ..................................... 9-168024

[51] Int. Cl.[7] ........................................................ A61F 5/00
[52] U.S. Cl. ............................... 602/16; 602/23; 602/24; 623/27
[58] Field of Search ................................. 602/23, 24, 16; 128/882; 122/882; 623/24, 25, 26, 27

[56] References Cited

U.S. PATENT DOCUMENTS

| 2,690,176 | 9/1954 | Nelson | 602/16 |
| 4,243,027 | 1/1981 | LaCourse | 128/80 |
| 5,728,164 | 3/1998 | Ferrari et al. | 623/31 |

*Primary Examiner*—Richard J. Apley
*Assistant Examiner*—Tam Nguyen
*Attorney, Agent, or Firm*—Rosenthal & Osha L.L.P.

[57] ABSTRACT

An orthotic apparatus for a paraplegic patient includes a pair of leg support members inclined toward each other at a predetermined inclination angle and a joint device coupled to an upper portion of each leg support member. The joint device allows rocking motion of the leg support members within a prescribed range such that the center of movement of the rocking motion approximates a virtual thigh joint rotation center point of the patient.

14 Claims, 4 Drawing Sheets

ORTHOTIC APPARATUS FOR PARAPLEGIC PATIENT

BACKGROUND OF THE INVENTION

1. Technical Field

This invention pertains to an orthotic apparatus used to help the walking of paraplegic patients, and especially related to a long leg brace where the long leg support member that braces the inferior limb (leg part) is connected at its upper part and each long leg support member is able to have rocking movements using the virtual thigh joint rotation center as a fulcrum.

2. Background Art

In the past, inferior limb braces for paraplegic patients have, as described in KOKAI (1994)-114089, had as its basis, a pelvic body trunk support member that fits around the pelvis of the wearer, and from this pelvic body trunk support member, there is a pillar shape long leg support member that supports both the left and right limbs. By this, they try to make the walking movement of the wearer smoother by making the rotation center of a rocking motion, when viewed from the side, to coincide with the thigh joint rotating central position of the wearer.

However, the above-mentioned items of the past have been over-sized in general as a device, and when one wanted to sit down on a wheel chair, the above-mentioned pelvic body trunk support member interfered, and had a problem of not allowing a smooth sitting position. In order to solve this problem, the purpose (subject) of this invention, is to present an orthotic apparatus that has no pelvic body trunk support member, is made of simple structure, and having a joint mechanism that gives a full support function for walking by the wearer.

In general, in one aspect, an orthotic apparatus for a paraplegic patient comprises a pair of leg support members inclined toward each other at a predetermined inclination angle; and a joint device coupled to an upper portion of each leg support member. The joint device allows rocking motion of the leg support members within a prescribed range such that the center of movement of the rocking motion approximates a virtual thigh joint rotation center point of the patient.

In another aspect, an orthotic apparatus for a paraplegic patient comprises a pair of leg support members inclined toward each other at a predetermined inclination angle and a joint device coupled to an upper portion of each leg support member to allow rocking motion of the leg support member such that the center of movement of the rocking motion approximates a thigh joint rotation center point of the patient. The joint device comprises a main block having opposing sides and rail members separated by an arc-shaped groove formed on each opposing side. A pair of carriers mounted on the opposing sides of the main block are coupled to the leg support members. Each carrier member has a main roller in rolling engagement with the arc-shaped groove and adapted to receive loading in a vertical direction and a plurality of side rollers adapted to roll on the rail members and to receive loading in a horizontal direction.

Other features and advantages of the invention will be made apparent by the following description and the appended claims.

DESCRIPTION OF THE PREFERRED EMBODIMENTS

Figure 1:
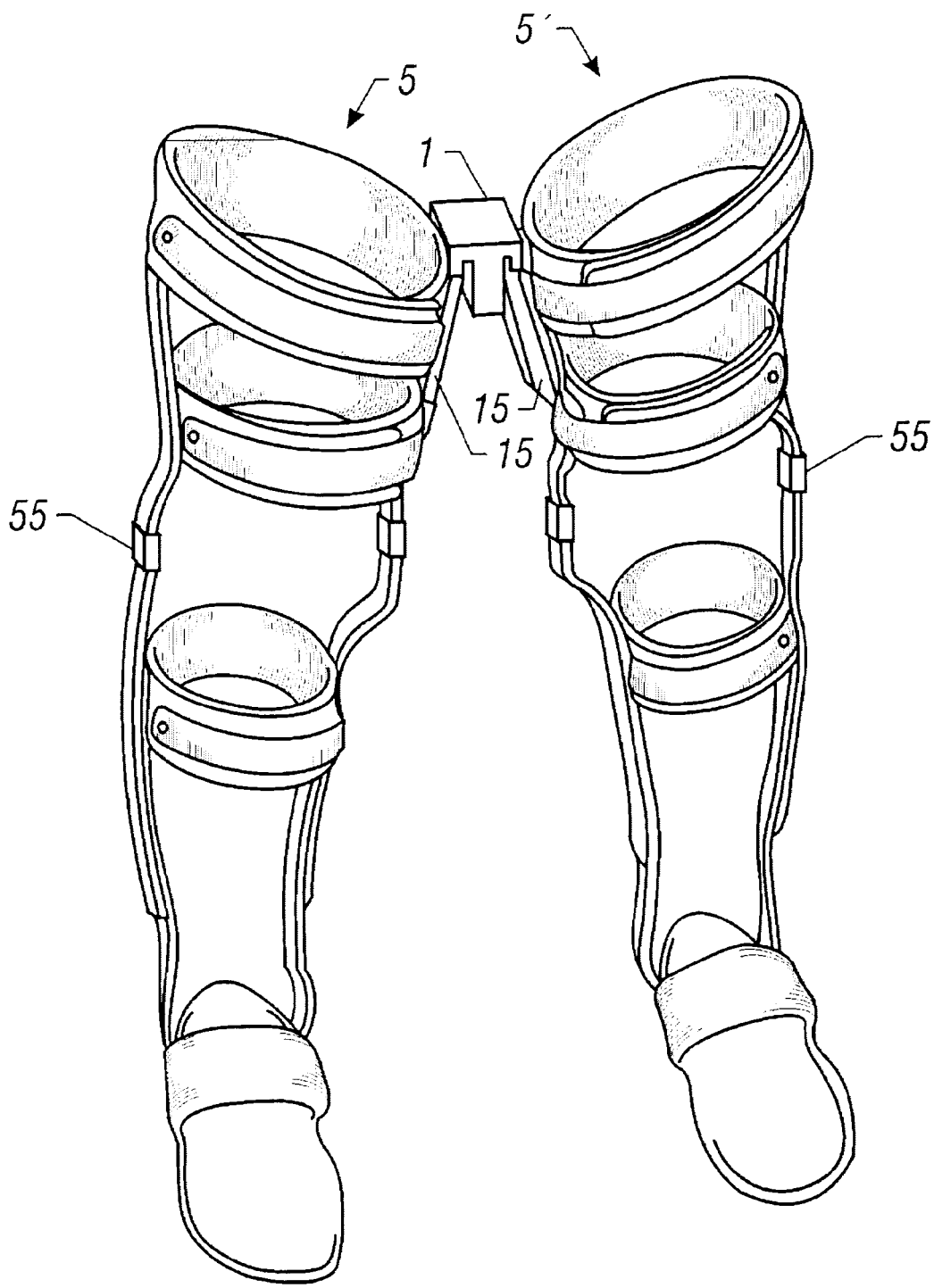
FIG. 1. Frontal drawings of the entire constitution of this invention
Figure 4:
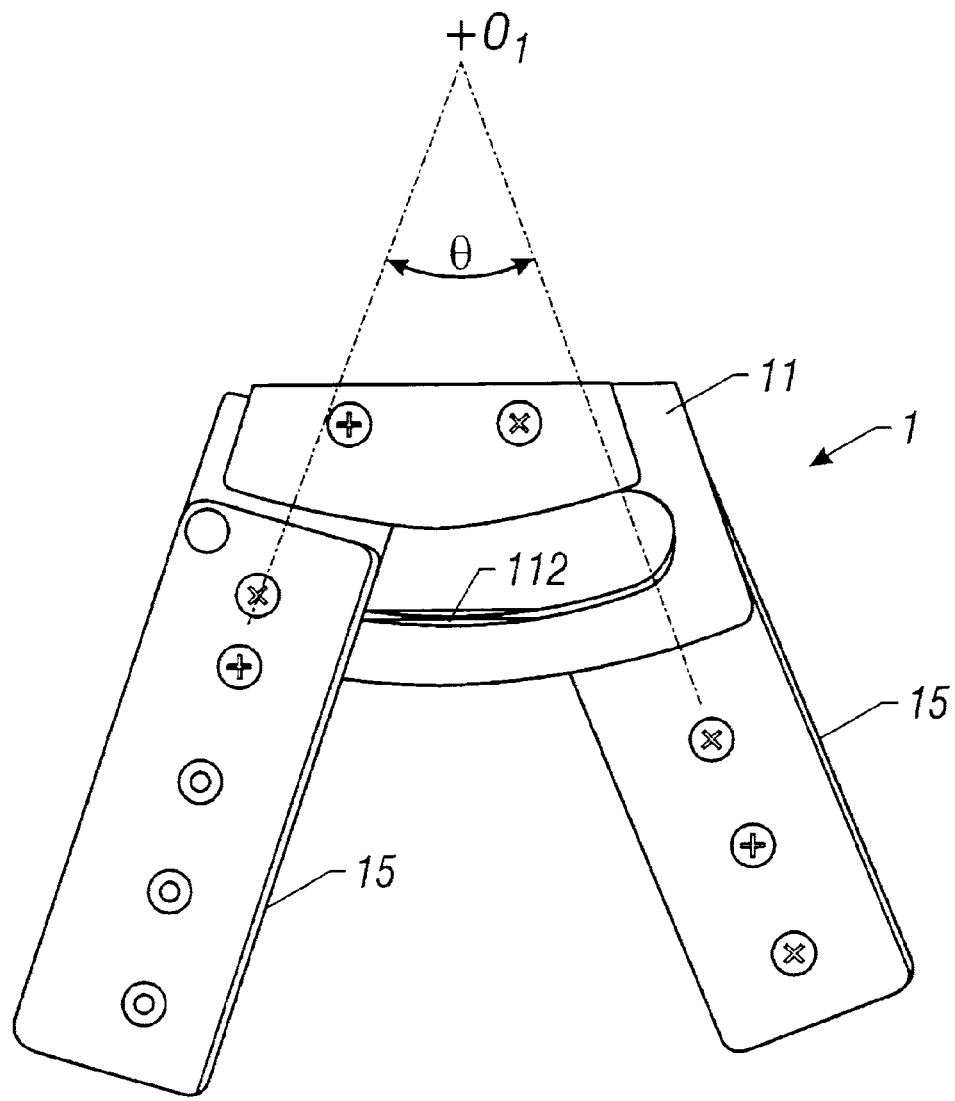
FIG. 4. Side view drawing showing action condition of the joint device of this invention.

For this invention's working form, we will explain it based on FIG. 1 or FIG. 4. An orthotic apparatus as shown in FIG. 1, comprises long leg support members 5 and 5' for supporting the entire inferior limb (leg part) of a patient, and a joint device 1 which supports and connects the upper ends of both above-mentioned long leg support members 5 and 5'. The joint device has a prescribed open angle (refer to FIG. 1), when viewed from the front, and a prescribed rocking angle (refer to FIG. 4), when viewed from the side, so that both the left and right long leg support members 5 and 5' are able to individually and separately have a rocking movement (forward movement).

The upper ends of the long leg support members 5 and 5' have attachments that connect to arms 15 (refer to FIGS. 2 and 3) that form part of the above-mentioned joint device 1. Through these attachments, the arms 15, described later, are assembled onto the long leg support members 5 and 5', and via arms 15, a rocking movement of the support members 5 and 5' are allowed with a pivot at the joint device 1. Also, at about the lengthwise centers of the leg support members 5 and 5' corresponding to the to the knee joint of the wearer, there is a joint mechanism 55, which is formed so as to be operated by a separate manipulation. Long leg support members 5 and 5', having such a joint mechanism 55, are similar to basic constitutions already in use.

Figure 2:
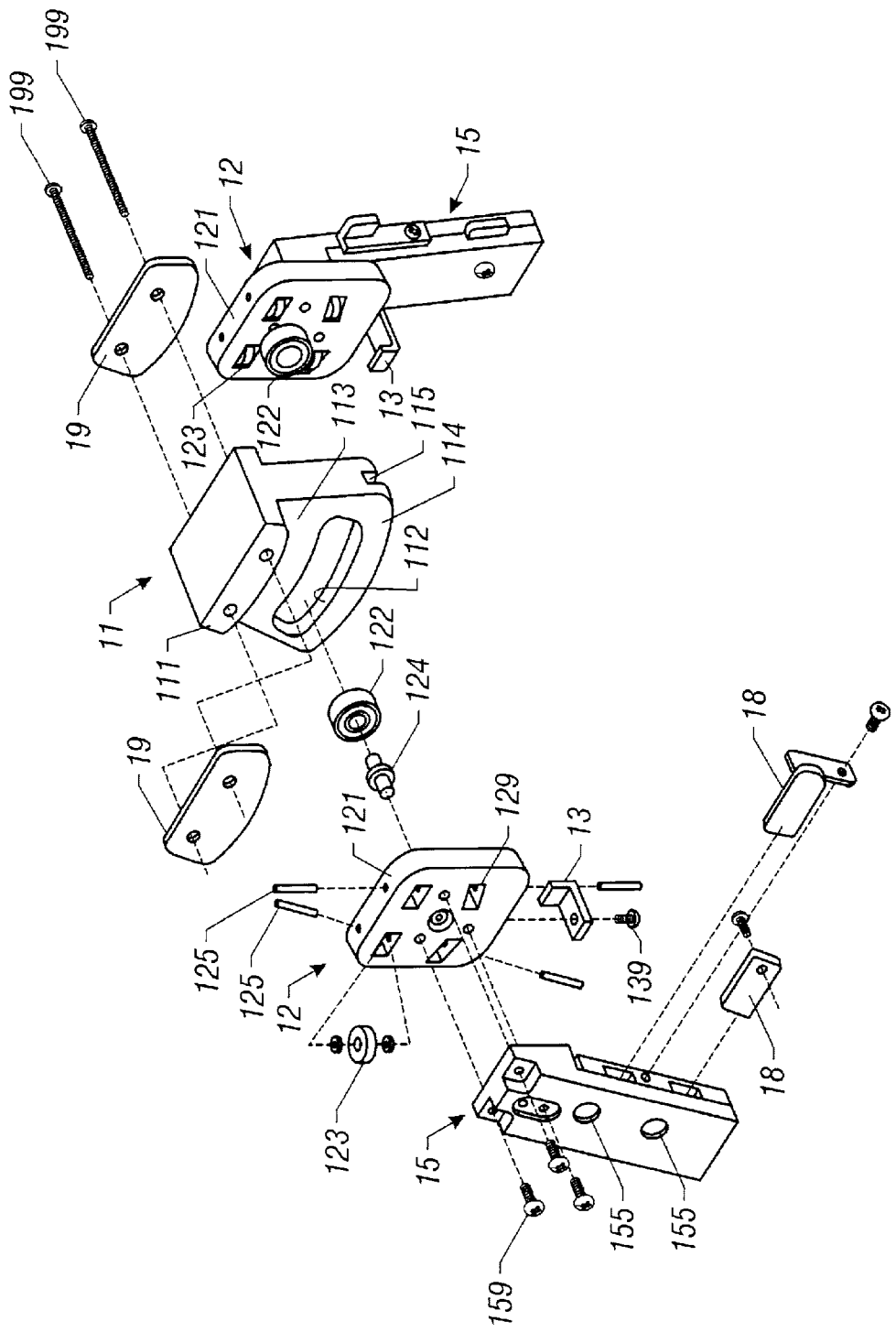
FIG. 2. An expanded diagonal drawing showing the overall constitution of the joint device that makes up the major part of this invention.

The long leg support members 5 and 5' are connected to the joint device 1 so that they have approximately 20 degrees open angle when viewed from the front, as shown in FIG. 2. The joint device 1 includes a main block 11 made of synthetic resin material (plastic material) such as polyacetyl resin (POM) etc., and carrier members 12 set in a symmetrical form on both sides of the main block 11 with an inclination angle of approximately 10 degrees to the arms 15 used in assembling the above mentioned long leg support members 5 and 5'.

Figure 3:
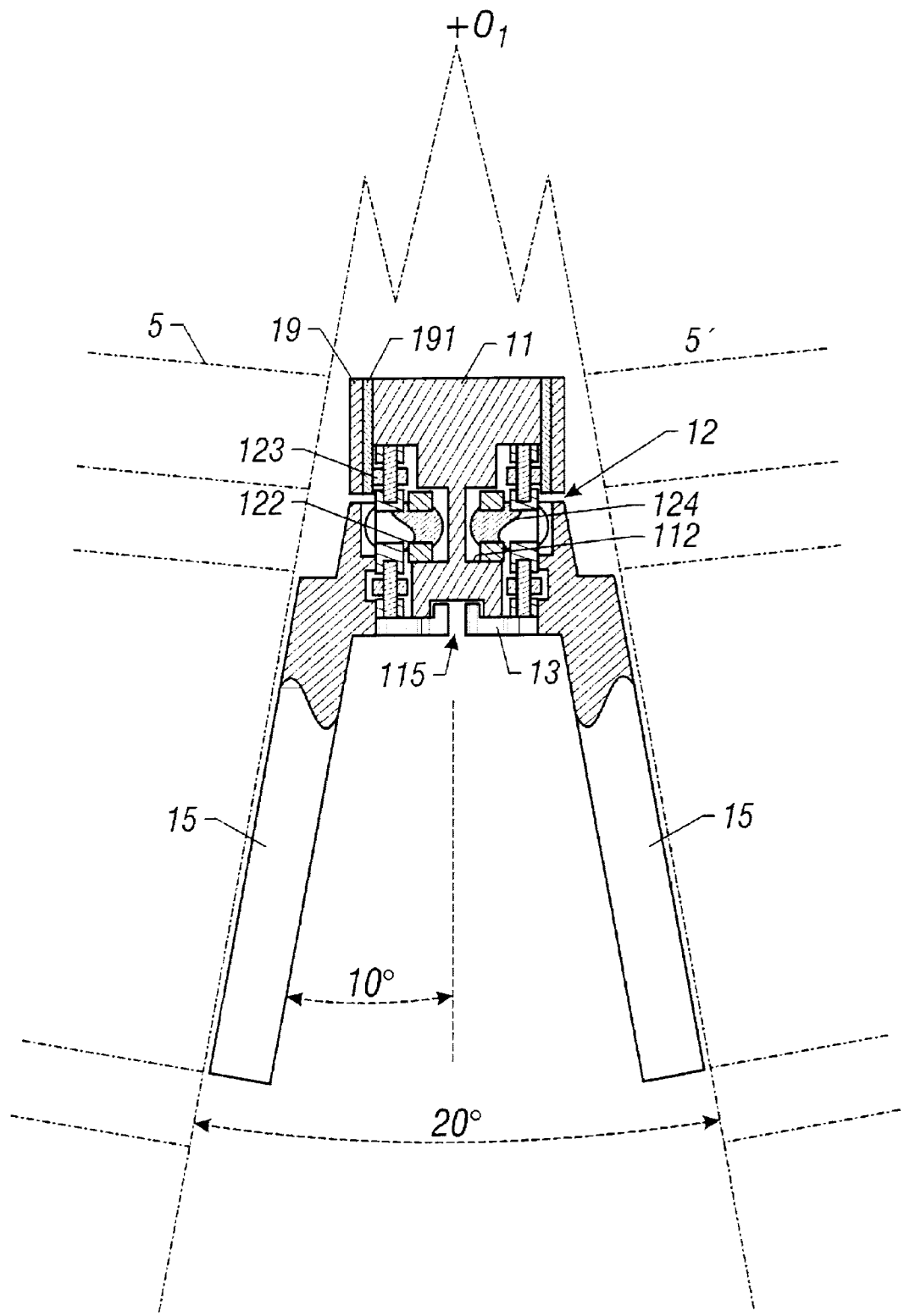
FIG. 3. Cross sectional drawing showing the overall constitution of t he joint device that makes up the major part of this invention.

The main block 11 is made in the form of a fan shape, and at the pivotal point of the fan, a base part 111 having a prescribed width (thickness) is .At the bottom part of the said base part 111 at the above-mentioned fan shaped part are arc-shaped grooves 112 (see FIGS. 2 and 3), made of similar shape, which engage main rollers 122 on the carrier members 12. The center (O1) of the arc of the arc-shaped groove 112, as shown in FIG. 4, is such that it will approximately fit at the virtual thigh joint rotation center of the wearer (patient) using this orthotic apparatus. Also, the arc angle (theta) of this arc-shaped groove 112 is fixed in the range of about 20 to 30 degrees (refer to FIG. 4). And, on the top and bottom of both arc-shaped grooves 112 having such a constitution, rail parts 113 and 114 are installed so that they line concentrically to the arc-shaped grooves 112. These rail parts 113 and 114, as shown in FIG. 3, engage the side rollers 123 on the carrier members 12, allowing the side rollers 123 to roll over rail parts 113 and 114. Also, at both sides of the above-mentioned base part 111 that forms the main block 11, there is a guide plate 19 that secures the carrier members 12 to the main block 11. The guide plates 19 are secured to the main block 11 by bolts 199. addition, on the inside of the above-mentioned guide plate 19, a plastic plate 191 is installed for the purpose of smooth rotating movement of the above-mentioned side rollers 123. Also, at the bottom part of this main block 11 of such constitution, as shown in FIG. 3, there is a stopper joining groove 115 which engages a stopper 13 that will limit the operation range (rocking angle) of the carrier member 12, and is to be described later.

The carrier members 12 at both sides of the main block 11 have a relative sliding movement with respect to main block 11. As shown in FIGS. 2 and 3, each carrier member 12 includes a base plate 121 having a certain thickness. Each carrier member is installed on the main block 11 at about the center of the base plate 121 and engages the arc-shaped groove 112 of the above-mentioned main block 11. Each carrier member is installed approximately symmetrically centered on the main roller 122, which bears the vertical directional load, and while making a rotational movement at the upper and lower rail parts 113 and 114 of the above-mentioned main block 11, and the side rollers 123, which share most of the horizontal directional loads. At the bottom part of base plate 121 that forms such a carrier member 12, there is a hook shaped part which includes the stopper 13, that engages the stopper joining groove 115 that is made at the bottom part of the above-mentioned main block 11. The stopper 13 is installed on the base plate 121 by a bolt 139.

The main roller 122, as shown in FIGS. 2 and 3, is installed so as to overhang from the said base plate 121, via shaft 124 with a flange mounted on the central part of the above-mentioned base plate 121. And such a main roller 122 engages to the arc-shaped groove 112 of the above-mentioned main block, and rotates within the arc-shaped groove. Also, side rollers 123 which are installed at right angles to the main roller 122, are installed via setting pins 125 etc. so as to rotate freely inside windows 129 of the above-mentioned base plate 121. The parts of the carrier member 12 above the main roller 122 are placed between the upper rail part 113 of the above-mentioned main block and guide plate 19, and is made to have rotating movements within the groove formed between the upper rail part 113 and the guide plate 19. The parts of the carrier member 12 installed below the above-mentioned roller 122, engage the bottom rail part 114 that is made into the above-mentioned main block 11, allowing rotating movement over the said rail part (lower rail part). Each of the rollers 122 and 123, are made of plastic material or metal material etc. such as steel, and in this working form, we considered strength and stiffness, and used miniature bearings made of steel.

Arm 15 which has sliding and rocking movements at both sides of the above-mentioned main block 11, and is attached onto the carrier member 12 of the above-mentioned constitution, is made of metal material having strong strength and stiffness. And, the arm 15 is installed onto the base plate 121 which forms the above-mentioned carrier member 12, by a connecting mechanism 159 such as bolts. In the working form, the above-mentioned inclination angle of the arm is about 10 degrees. And onto the arm 15 with such a constitution, there are multiple number of fixing holes 155, used for fixing the above-mentioned long leg support member 5, and around the fixing holes 155, a lock member 18 used in fixing the above mentioned long leg support member 5. Via such an arm 15 having such an inclination angle, the left and right long leg support members 5 and 5' are installed onto the above-mentioned joint device 1, and the opening angle, when viewed from the front, is prescribed as to be about 20 degrees (Refer to FIG. 3).

The disclosed orthotic apparatus has several advantages. First it becomes possible for a paraplegic patient wearing such an orthotic apparatus in parallel with an assistance device, such as a crutch etc., to perform an alternating walking step. In other words, the wearer, by moving his hips sideways, using the joint device 1 as a pivot can become able to move forward one of the braced legs (inferior limb) with the long leg support member 5. The joint device 1, as shown in FIG. 1, having a prescribed opening angle (about 20 degrees) and each long leg support members 5 and 5' being set so as to have the central position of the rocking movement come close to the rotating center point of the virtual thigh joint of the wearer (point O1 in FIG. 4), allows the above-mentioned long leg support members 5 and 5', i.e., the inferior limb, to make a smooth forward moving motion. Also, by each long leg support member 5 and 5' moving the left and right inferior limb forward, each separately and independently, using the above-mentioned joint device I as a pivotal point, each left and right inferior limb (leg part) can make a forward movement smoothly. Another advantage is that the above-mentioned joint device 1 is placed between the thighs of the wearer and is the type that does not require a pelvic body trunk support member as done in the past. Thus there are no elaborate devices around the pelvis, and this allows one to sit smoothly onto a wheel chair, etc.

Also, the joint device 1 that operates in this working form, as shown in FIG. 2 and FIG. 3, is centered on the main block 11, and on both sides of the main block 11 are carrier members 12 which conduct sliding movements and arms 15 which are installed at a prescribed inclination angle to both carrier members 12. And, on each of the above-mentioned carrier member 12, there is a main roller 122 and multiple numbers of side rollers 123 which allow, the carrier member 12, to have a smooth movement relative to the main block 11. Thus, both the left and right long leg support member 5 and 5' that are attached to carrier member 12 can, using the above-mentioned main block 11 as a pivotal point, produce a smooth sliding and rocking motion at both sides of the main block 11. In other words, each left and right inferior limb (leg part) supported by both long leg support members 5 and 5' can conduct a smooth forward movement.

The rollers 122 and 123 on the carrier member 12 are made to have relative movement (rotating movement) over the arc-shaped groove 112, formed on the main block 11 or on the rail parts 113 and 114. Also, the arc's central point (O1 point in FIG. 4) of the above-mentioned arc-shaped groove 112, where the main roller 122 has a rotating movement, and of the rail parts 113 and 114, are to approximately match, when viewed from the side, the virtual thigh joint rotating center point of this orthotic apparatus wearer. Thus, the rotation central point of the rocking movement for the carrier member 12 and the carrier member 12 with above-mentioned arm 15 are to approximately match the thigh joint rotation center point (when viewed from the side). As a result, the feeling for forward movement of the inferior limb (leg part) of the wearer of this orthotic apparatus approximately matches the rocking movement of the long leg support members 5 and 5' that brace the inferior limb (leg part). Thus, the wearer, becomes able to have a smooth inferior limb forward movement with a sense of no incongruity.

The main block 11 which is the basis of action of the joint device 1, is made of plastic material having a high surface hardness and a low friction constant, and upon designing a reduction of weight of the main block 11, one can conduct a smooth relative movement between said main block 11 and carrier member 12. As a result, one is able to have a smooth rocking movement of the long leg support members 5 and 5' that are joined via arms 15 to the above-mentioned carrier members 12, allowing a smooth forward movement of the inferior limb (leg part) of the wearer. Also, one can reduce the weight and size of the main block 11 and can design the reduction of size and weight of the overall joint device 1. As a result, one can improve the wearability of this apparatus (orthotic apparatus).

According to this invention, an orthotic apparatus for use in helping walking of paraplegic patients, includes long leg support members which support the entire inferior limb of the wearer, and the upper parts of the long leg support members are maintained at a prescribed inclination angle (open angle) and are is supported so as to enable rocking movement within a prescribed range, of the long leg support members. Each long leg support member rocks separately and independently, with the rocking movement central point designed to approximately match the virtual thigh joint rotating center of the wearer. This allows paraplegic patients wearing this orthotic apparatus, in conjunction with an assistant device, such as crutches, to conduct a smooth alternating walking step. In other words, the wearer by moving his hip sideways, can move forward, where one part of the leg (inferior limb) braced with the long leg support member uses the joint device made on the upper part of this long leg support member as a pivot and conducts an alternating movement which enables the person to make alternating steps. At the same time the joint device, when viewed from the front, is set to have a prescribed open angle, and for each long leg support member, the center position of its rocking movement is set so that it comes close to the rotation center of the imaginary thigh joint of the wearer, and thus allowing the forward movement of the long leg support member, i.e., the inferior limb, to become smooth. Also, by having the left and right long leg support members moving separately and independently with the above-mentioned joint device as a pivot, each left and right inferior limb's (leg part) forward movement action could be made smoothly and independently for the left and right limbs. Also, in this invention, the joint device is arranged between the thighs of the wearer and is not the type that requires a pelvic body trunk support apparatus thus, there are no elaborate parts around the pelvis and the sitting onto wheel chairs etc. becomes smoother.

What is claimed is:

1. An orthotic apparatus for a paraplegic patient, comprising:
    a pair of leg support members inclined toward each other at a predetermined inclination angle; and
    a joint device coupled to an upper portion of each leg support member, the joint device comprising a main block and a pair of carrier members slidably mounted on opposite sides of the main block, the main block comprising rail members separated by an arc-shaped groove on each of the opposite sides, each carrier member comprising a main roller in rolling engagement with the arc-shaped groove and a plurality of side rollers adapted to roll on the rail members, and a pair of arms connecting each carrier member to one of the leg support members, the arms being adapted to provide the predetermined inclination angle between the leg support members, the joint device allowing rocking motion of the leg support members within a prescribed range such that the center of movement of the rocking motion approximates a virtual thigh joint rotation center point of the patient.

2. The orthotic apparatus of claim 1 wherein the main block includes a stopper groove and each carrier member includes a stopper member which engages the stopper groove, the stopper groove and the stopper member being arranged to limit the rocking motion of each leg support member.

3. The orthotic apparatus of claim 1, wherein the main block is formed of a synthetic resin.

4. An orthotic apparatus for a paraplegic patient, comprising:
    a pair of leg support members inclined toward each other at a predetermined inclination angle; and
    a joint device coupled to an upper portion of each leg support member to allow rocking motion of the leg support member such that the center of movement of the rocking motion approximates a virtual thigh joint rotation center point of the patient, the joint device comprising:
    a main block having opposing sides and rail members separated by an arc-shaped groove formed on each opposing side; and
    a pair of carrier members mounted on the opposing sides of the main block and coupled to the leg support members, each carrier member having a main roller in rolling engagement with the arc-shaped groove and adapted to receive loading in a vertical direction, each carrier member having a plurality of side rollers adapted to roll on the rail members and to receive loading in a horizontal direction.

5. The orthotic apparatus of claim 4, wherein the main block includes a stopper groove and each carrier member includes a stopper member and wherein the stopper and stopper member cooperate to limit the rocking motion of the leg support member within the prescribed range.

6. The orthotic apparatus of claim 3, wherein the synthetic resin material is a polyacetyl resin.

7. An orthotic apparatus for a paraplegic patient, comprising:
    a pair of leg support members; and
    a joint device coupled to an upper portion of each leg support member, the joint device comprising a main block having arc-shaped grooves formed on opposite sides of the main block, and a pair of carrier members slidably mounted on the opposite sides of the main block, each carrier having a main roller in rolling engagement with one of the arc-shaped grooves, each carrier member being coupled to one of the leg support members to allow rocking motion of the leg support members within a prescribed range such that the center of movement of the rocking motion approximates a virtual thigh joint rotation center point of the patient.

8. The orthotic apparatus of claim 7, wherein the joint device includes a pair of arms, each arm connecting one of the leg support members to one of the carrier members, the arms being adapted to provide a predetermined inclination angle between the leg support members.

9. The orthotic apparatus of claim 7, wherein each of the opposite sides of the main block includes rail members separated by the arc-shaped groove and each carrier member includes a plurality of side rollers adapted to roll on the rail members.

10. The orthotic apparatus of claim 9, wherein the main block includes a stopper groove and each carrier member includes a stopper member which engages the stopper groove, the stopper groove and stopper member being arranged to limit the rocking motion of each leg support member.

11. An orthotic apparatus for a paraplegic patient, comprising: a pair of leg supporting members; and
    a joint device coupled to an upper portion of each leg support member, the joint device comprising a main block having arc-shaped grooves formed on opposite sides of the main block;

a pair of carrier members slidably mounted on the opposite sides of the main block, each carrier member having a main roller in rolling engagement with the arc-shaped groove and being coupled to one of the leg support members to allow rocking motion of each leg support member within a prescribed range, wherein the upper most portion of the leg support members defines the uppermost portion of the orthotic apparatus.

12. The orthotic apparatus of claim 11, wherein the joint device further comprises a pair of arms, each arm connecting one of the carrier members to one of the leg support members.

13. The orthotic apparatus of claim 12, wherein each of the opposite sides of the main block includes rail members separated by the arc shaped groove and each carrier member includes a plurality of side rollers adapted to roll on the rail members.

14. The orthotic apparatus of claim 12, wherein the main block includes a stopper groove and each carrier member includes a stopper member which engages the stopper groove, the stopper grove and the stopper members being arranged to limit the rocking motion of each leg support member.

* * * * *